(12) United States Patent
Vija et al.

(10) Patent No.: US 7,825,383 B2
(45) Date of Patent: Nov. 2, 2010

(54) MOBILE CAMERA FOR ORGAN TARGETED IMAGING

(75) Inventors: A Hans Vija, Evanston, IL (US); James T. Chapman, Glen Ellyn, IL (US); Peggy Hawman, Schaumburg, IL (US); Ansgar Graw, Chicago, IL (US); John Thomas Pawlak, Villa Park, IL (US); Guenter Hahn, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 148 days.

(21) Appl. No.: 11/524,798

(22) Filed: Sep. 21, 2006

(65) Prior Publication Data

US 2008/0073541 A1 Mar. 27, 2008

(51) Int. Cl.
*G01T 1/166* (2006.01)
(52) U.S. Cl. ............... 250/363.05; 250/363.04; 378/11; 378/17; 378/175
(58) Field of Classification Search ............ 378/11, 378/17, 178, 15, 197, 196, 195, 62, 21, 4, 378/13; 250/363.05, 363.08, 363.04, 370.08
See application file for complete search history.

(56) References Cited

U.S. PATENT DOCUMENTS

| | | | |
|---|---|---|---|
| 2,862,333 A * | 12/1958 | Gardiol | ........... 446/444 |
| 5,519,222 A | 5/1996 | Besett | |
| 5,523,571 A * | 6/1996 | Velazquez et al. | ...... 250/363.05 |
| 5,923,038 A | 7/1999 | DiFilippo et al. | |
| 6,147,352 A * | 11/2000 | Ashburn | ........... 250/363.05 |
| 6,150,662 A | 11/2000 | Hug et al. | |
| 6,211,523 B1 | 4/2001 | Gagnon | |
| 6,388,244 B1 | 5/2002 | Gagnon | |
| 6,595,704 B2 * | 7/2003 | Ambrose | ............ 396/428 |
| 6,664,542 B2 | 12/2003 | Ye | |
| 6,774,371 B2 | 8/2004 | Garrard et al. | |
| 6,927,395 B2 | 8/2005 | Koops et al. | |

(Continued)

FOREIGN PATENT DOCUMENTS

WO    WO2004096050    *    4/2004

(Continued)

OTHER PUBLICATIONS

Hawman, et al. "The Cardiofocal collimator: a variable-focus collimator for cardiac SPECT", 1994, Phys. Med. Biol., vol. 39, pp. 439-450.*

(Continued)

*Primary Examiner*—David P Porta
*Assistant Examiner*—Yara B Green
(74) *Attorney, Agent, or Firm*—Peter Kendall

(57) ABSTRACT

A mobile detector system for use in the detection of radiation photons. The detector system includes an exterior casing, having an internal area. The internal area has an interior periphery and an exterior periphery, at least one rail, at least one mobile camera, that is movably mounted on the at least one rail, and at least one motor. The motor drives at least one mobile camera, and the at least one mobile camera is movable along at least one rail within the exterior casing, to a plurality of radiation receiving positions.

28 Claims, 6 Drawing Sheets

U.S. PATENT DOCUMENTS

| | | | | |
|---|---|---|---|---|
| 7,105,825 B2* | 9/2006 | Juni | | 250/363.04 |
| 7,108,421 B2* | 9/2006 | Gregerson et al. | | 378/197 |
| 7,242,002 B2 | 7/2007 | Blevis et al. | | |
| 7,297,956 B2* | 11/2007 | Fenster et al. | | 250/363.08 |
| 7,465,930 B2* | 12/2008 | Joung | | 250/363.05 |
| 2003/0111608 A1* | 6/2003 | Dulmen et al. | | 250/363.1 |
| 2003/0230724 A1* | 12/2003 | Koops et al. | | 250/363.08 |
| 2004/0013225 A1* | 1/2004 | Gregerson et al. | | 378/19 |
| 2004/0013239 A1* | 1/2004 | Gregerson et al. | | 378/197 |
| 2004/0042582 A1* | 3/2004 | Ein-Gal | | 378/8 |
| 2004/0251419 A1* | 12/2004 | Nelson et al. | | 250/370.09 |
| 2004/0262525 A1* | 12/2004 | Yunker et al. | | 250/363.08 |
| 2006/0056581 A1* | 3/2006 | Hoffman et al. | | 378/19 |
| 2006/0180766 A1 | 8/2006 | DiFilippo et al. | | |
| 2006/0202650 A1* | 9/2006 | Hausner et al. | | 318/268 |
| 2008/0073539 A1 | 3/2008 | Vija | | |
| 2008/0073540 A1 | 3/2008 | Vija | | |
| 2010/0142671 A1* | 6/2010 | Gregerson et al. | | 378/19 |

FOREIGN PATENT DOCUMENTS

| WO | WO2004096050 A1 | 11/2004 |
|---|---|---|

OTHER PUBLICATIONS

Palmer et al. "Pinhole emission computed tomography: method and experimental evaluation", 1990, Phys. Med. Biol., vol. 35, No. 3, pp. 339-350.*

"O-Arm Imaging System" Medgadget, Retrieved [Dec. 11, 2008], Retrieved from URL: <medgadget.com/archives/print/002335print.html>, Published [Jul. 10, 2006].*

Hawman, et al. "The Cardiofocal collimator: a variable-focus collimator for cardiac SPECT", 1994, Phys. Med. Biol., vol. 39, pp. 439-450.

Palmer et al., "Pinhole emission computed tompgraphy: method an experimental evaluation", 1990, Phys. Med. Biol., vol. 35, No. 3, pp. 339-350.

Keyes, "Computed Tomography in Nuclear Medicine", Computer Methods, C.V. Mosely, St. Louis, 1977, pp. 130-138.

Orlov, "Theory of three dimensional reconstruction II: the recovery of operator", Soviet Phys Crystallogr., 20:429-433 (1976).

Natterer, et al., "Mathematical Methods in Image Reconstruction", SIAM, Philadelphia, Pa. (2001).

"O-Arm Imaging System", Medgadget, Retrieved [Mar. 4, 2010], retrieved for URL: <medgadget.com/archives/print/002335print.html>, Published [Jul. 10, 2006].

* cited by examiner

MOBILE CAMERA FOR ORGAN TARGETED IMAGING

BACKGROUND OF THE INVENTION

1. Field of the Invention

The invention relates to a mobile camera implementation for a medical imaging device such as a gamma camera, and more particularly a device having fully enclosed one or more camera detectors that move within the device housing on rails.

2. Background Discussion

Single photon emission computed tomography (SPECT) imaging is performed by using a gamma camera to acquire image or projection data from multiple angles with respect to a patient. The data is then sent to a computer that applies a tomographic reconstruction algorithm to the multiple projections, yielding a 3D dataset, which can be used to generate tomographic images for display on a display device.

To acquire SPECT images the gamma camera is rotated around the patient with projections being acquired at defined points during the rotation, typically every 3-6 degrees. In most cases, a full 360 degree rotation is used to obtain an optimal reconstruction. The time taken to obtain each projection is also variable, but 15-20 seconds is typical giving a total scan time of 15-20 minutes.

Multi-headed gamma cameras can provide accelerated acquisition, e.g. a dual headed camera can be used with heads spaced 180 degrees apart, allowing 2 projections to be acquired simultaneously, with each head only requiring 180 degrees of rotation. Triple-head cameras with 120 degree spacing are also used.

Gated acquisitions are possible with SPECT, just as with planar imaging techniques such as multiple gated acquisition scans (MUGA). Cardiac gated myocardial SPECT can be used to obtain quantitative information about myocardial perfusion during the cardiac cycle, thickness and contractility of the myocardium and allow calculation of left ventricular ejection fraction, stroke volume, and cardiac output.

Computer tomography (CT) scanners use a fan shaped beam of x-rays that is directed to an array of detectors that are fixed in position relative to the x-ray source. In some models of CT devices the images are acquired by a "translate-rotate" method in which the x-ray source and the detector in a fixed relative position move across the patient followed by a rotation of the x-ray source/detector combination (gantry) by one degree. In other models, instead of a row of detectors that move with the X-ray source, a stationary 360 degree ring of detectors is provided. The fan shaped x-ray beam is rotated around the patient in a non-fixed relationship with respect to the stationary detectors.

Ultrasonography is a useful ultrasound-based medical imaging technology used for medical diagnostics. In addition to its diagnostic value, ultrasonography can be used to treat benign and malignant tumors and other disorders through focused ultrasound surgery (FUS) or high intensity focused ultrasound (HIFU).

Positron emission tomography (PET) is a nuclear medicine medical imaging technique that produces three dimensional images using a radioactive tracer isotope, and is based on the physical phenomenon whereby annihilation of a positron by collision with an electron results in the simultaneous emission of two gamma photons traveling in 180 degree opposed directions. The simultaneously emitted photons are detected by a pair of 180 degree opposed detectors within the camera unit, by detecting coincidence events.

The devices required for the above medical applications are generally large and extremely expensive. Some of the smaller devices run on gantry systems that are open exposing the patient to the moving cameras and mechanics. The size and/or or movement of the devices during the procedure can be intimidating to a patent, adding stress to an already stressful situation. To date, a simple enclosing of the gantry to eliminate motion is possible but sub-optimal for patient positioning. Additionally, enclosing the detector heads is costly, as the detector heads are usually suspended from a gantry or from an arm where the motion of the detectors is enabled by various trunions.

SUMMARY OF THE INVENTION

The present invention provides a variety of advances and improvements over, among other things, the prior art systems and methods, by providing an enclosed mobile camera unit that can be constructed in various sizes to enable the technology to be used for heretofore difficult treatments.

In one embodiment of the invention a detector system is used in the reception and translation of radioactive wavelengths. The detector system has an exterior casing including an internal area. The internal area houses one or more rails in a fixed position within the internal area, at least one mobile camera, and at least one motor for driving a mobile camera or cameras.

In another embodiment of the invention, at least one mobile camera is movable along at least one rail within an exterior casing of a detector system. The camera is moved on a rail or rails to a plurality of radioactive wavelengths receiving positions.

In a further embodiment of the invention, a detector casing is rotatably affixed to a chair. The detector casing houses a mobile camera that is movable along at least one rail within the casing of the detector system. The camera is moved on a rail or rails to a plurality of radioactive wavelengths receiving positions.

In another embodiment of the invention, a detector casing is rotatably affixed to a stand. The detector casing houses a mobile camera that is movable along at least one rail within the casing of the detector system. The camera is moved on a rail or rails to a plurality of radioactive wavelengths receiving positions.

In a further embodiment of the invention detector system includes a casing that houses a rail or rails that are at least partially flexible.

In a still further embodiment of the invention a detector system includes a casing that houses a rail or rails that have a flexible region and a non-flexible region.

In another embodiment of the invention a detector system includes a casing that houses a rail or rails that has flexible end portions and a rigid center portion.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

BRIEF DESCRIPTION OF THE DRAWINGS

The preferred embodiments of the present invention are shown by way of example, and not limitation, in the accompanying figures, in which.

DETAILED DESCRIPTION OF THE INVENTION

Figure 1:
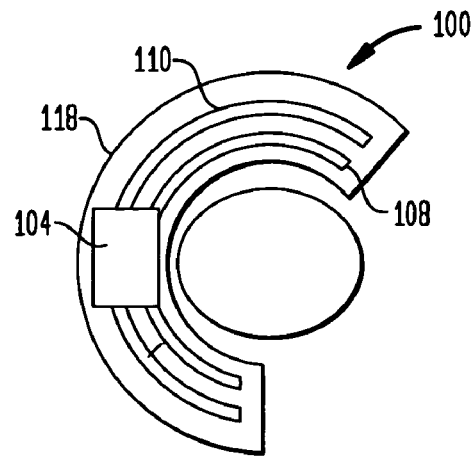
FIG. 1 is a cross-sectional top view of the detector system in accordance with the present invention.

While the present invention may be embodied in many different forms, a number of illustrative embodiments are described herein with the understanding that the present disclosure is to be considered as providing examples of the principles of the invention and that such examples are not intended to limit the invention to preferred embodiments described herein and/or illustrated herein.

It is advantageous to define several terms before describing the invention. It should be appreciated that the following definitions are used throughout this application.

DEFINITIONS

Where the definition of terms departs from the commonly used meaning of the term, applicant intends to utilize the definitions provided below, unless specifically indicated.

For the purposes herein the term "arc, arced, arched" refers to a continuous section of any curve.

For the purposes of the present invention, the term "detector" refers to any material or device capable of recognizing and translating the photons released by a radioactive material. This can include crystals, hyperpure germanium, solid-state detectors, etc.

For the purposes of the present invention, the term "detector system" refers to any group of devices that enable the reception and translation of radioactive wavelength. This includes, but is not limited to, housings, mobile cameras, rails, detectors, stands, chairs, beds, etc. that are used in conjunction with nuclear medicine.

For the purposes of the present invention, the term "mobile camera" refers to any type of unit that contains the components to receive and translate radioactive wavelengths. These components can include crystals, photomultipliers, collimators, solid state detectors, housings, electrical components, motors, etc.

For the purposes of the present invention, the term "tomography" refers to any imaging technique using gamma rays that provides information presented as cross-sectional slices through the patient and can be reformatted and manipulated by computer as required.

For the purposes of the present invention, the term "subject" refers to any living or non-living organism, as well as any organic or inorganic substance that be penetrated with any type of wavelength.

For the purposes of the present invention, the term "flexible" refers to a structure that is capable of being bent or flexed, repeatedly without injury or damage, is responsive to change and is adaptable.

For the purposes of this invention the term "trunion" refers to a cylindrical protrusion used for mounting an object to permit rotation.

For the purposes of this invention, the term "turret" refers to any device that facilitates both horizontal and vertical movement.

Discussion of the Preferred Embodiments

The disclosure relates to a mobile gamma camera enclosed in a stationary outer casing. The design is applicable to all detector technologies such as ultrasonography (US), solid-state detectors (e.g., CZT), photomultiplier tubes, etc., and collimation schemes such as parallel, focusing, multi-focusing, variable focusing and other adaptive collimation schemes that are mobile in accordance with the teachings herein. The applicability of technologies that are currently available, or come to be available in the future, will be evident to those skilled in the art.

The detector system disclosed herein can be used to design various tomographic gamma cameras enabling SPECT, CT, PET or US for various applications, such as for cardiac, prostate, brain, extremities, and oral cancer imaging. Examples of these designs are illustrated and described hereinafter, however they are not intended to limit the scope of the invention and are to be considered examples of the potentials of the disclosed system.

Figure 2:
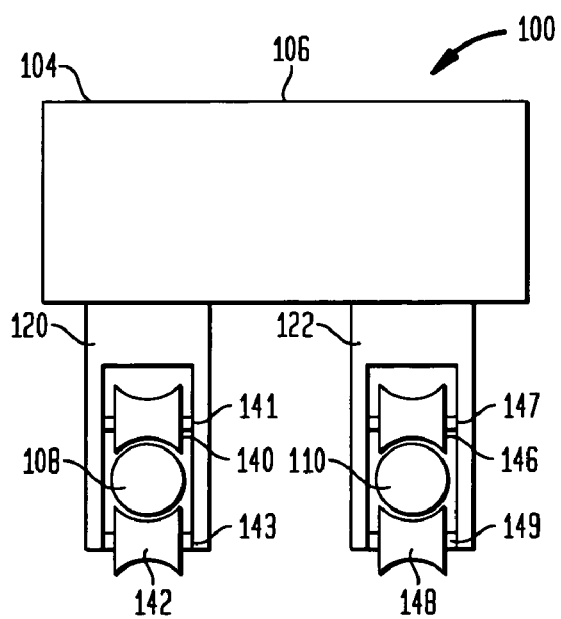
FIG. 2 is an end view of the mobile camera unit in accordance with the present invention.
Figure 3:
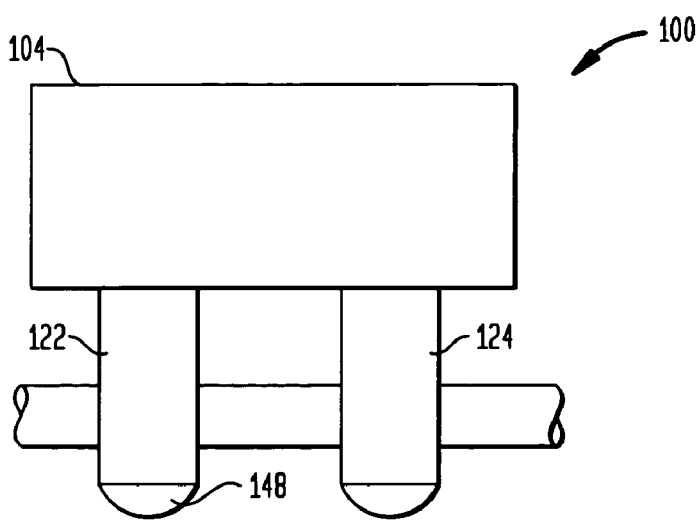
FIG. 3 is a side view of the mobile camera unit in accordance with the present invention.

In one embodiment a gamma camera system is indicated generally as 100 in FIGS. 1, 2 and 3, wherein mobile gamma cameras 104 are self contained units that move on a pair of rails including inner rail 108 and outer rail 110 inside a housing 118. The housing 118 can be part of an overall support structure or can be an independent, stand alone unit. Whether part of an overall support structure or independent unit, the housing 118, the support structure and/or surrounding area, are preferably shielded to minimize detector exposure of radiation from extraneous sources.

The mobile gamma camera 104, in this embodiment, has four (4) supports, (three of which, 120, 122 and 124, are collectively shown in FIGS. 2 and 3), that rigidly extend from the body 106 and contain wheel pairs 140 and 142, and 146 and 148 respectively. Wheels 140 and 142 are maintained within the support 120 by shafts 141 and 143 respectively. Wheels 146 and 148 are maintained within support 122 by shafts 147 and 149 respectively. Support 124 and the corresponding support not visible in an end view, have identical wheel pairs.

The wheel pairs 140 and 142 and 146 and 148 run on inner rail 108 and outer rail 110 and are powered either by individual motors or, more preferably by a single motor. The individual motors can be located in the supports 120, 122, 124 and corresponding support not visible in the views, or in the body 106 of the mobile gamma camera 104. If a single, geared motor is used, it can be placed in the body 106.

The gamma camera system 100 illustrated in FIG. 1 incorporates a single mobile gamma camera 104, however the number of mobile gamma cameras 104 is only limited by geometric considerations. The motion of the detector heads is then appropriately limited.

Figure 4:
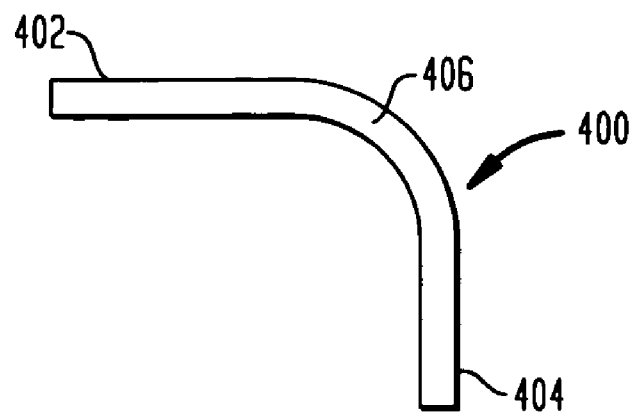
FIG. 4 is a top view of a rail having inflexible and flexible portions in accordance with the present invention.

The 108 and 110 rails can be rigid, flexible or segmented to provide both flexible and inflexible portions, as illustrated in FIG. 4. The advantage to the flexible, or partially flexible, rails is to achieve an optimally close track for a range of subject sizes.

In FIG. 4 the rail 400 is segmented with rigid ends 402 and 404 and flexible center 406. This configuration by way of example only and other combinations and configurations will be evident to those skilled in the art.

Figure 5:
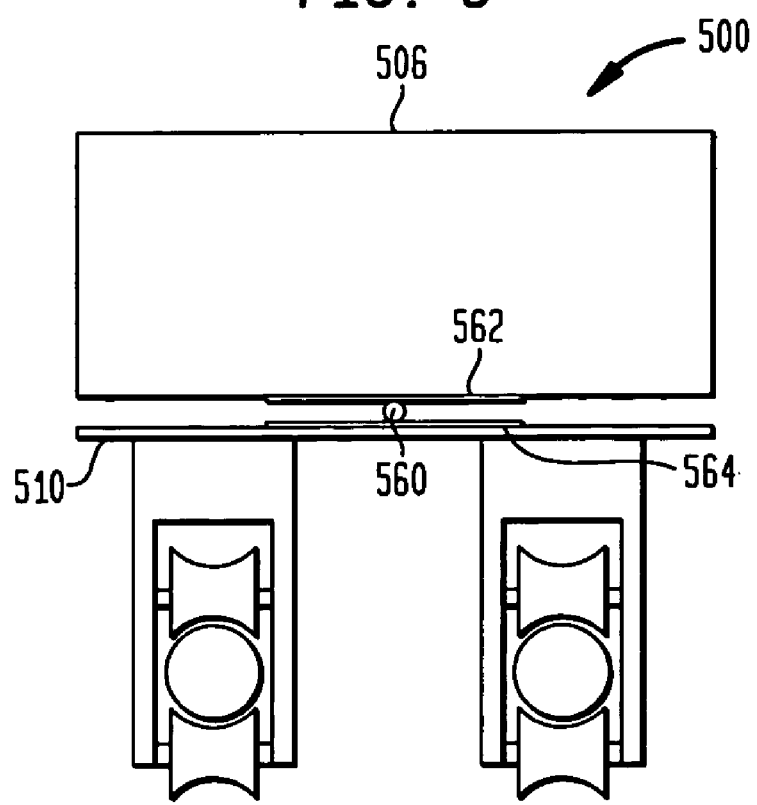
FIG. 5 is an end view of the mobile camera unit having a turret between the base and camera unit in accordance with the present invention.

Referring to FIG. 5, in some applications it is advantageous for the body 506 of the mobile gamma camera 500 to swivel or rotate in order to achieve optimal tomographic sampling. In the mobile gamma camera 500, as illustrated in FIG. 5, a turret 560 is placed between the body 506 and the wheelbase 510. The body 506 can swivel vertically about 10° to 20°, and can translate perpendicular to the detector face. On the horizontal plane the body 506 can swivel up to 360° and the amount of horizontal movement required will be evident to those skilled in the art. In the embodiment illustrated herein, support plates 562 and 564 have been added to provide additional reinforcement. Other methods of providing either horizontal or vertical rotation or both will be known to those skilled in the mechanical arts.

Figure 6:
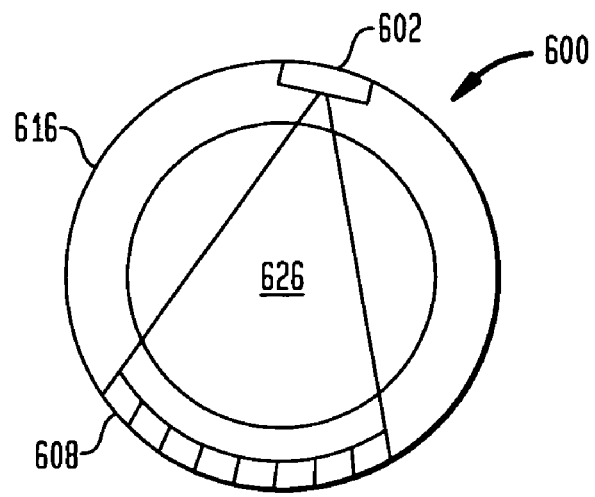
FIG. 6 is a cross-sectional top view of an embodiment of the detector system arranged for a CT scan in accordance with the present invention.
Figure 7:
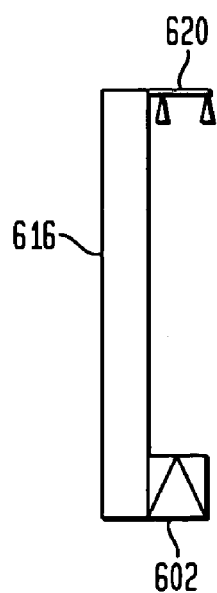
FIG. 7 is a fragmentary cross-sectional side view of the housing of the detector system of FIG. 6 in accordance with the present invention.
Figure 8:
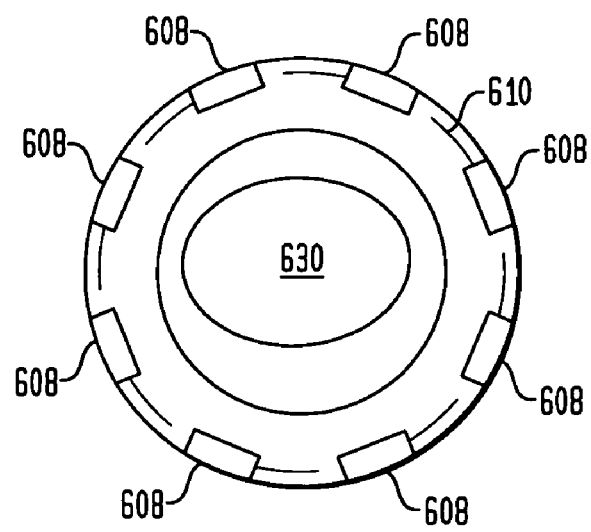
FIG. 8 is a cross-sectional top view of the embodiment of FIG. 6 arranged for a SPECT scan in accordance with the present invention.

In FIGS. 6, 7, and 8, an alternate embodiment 600 is illustrated using the track system disclosed herein for a scanning system using a radiation source 602 that is affixed to a slip ring 616. The opposing side of the slip ring 616 has a pair of rails 620 that carry detectors 608. The detectors 608 can be positioned along the rails 620 in either a stationary configuration or they can rotate around the rails 620.

In FIG. 6, the detectors 608 are stationary and within the field of view 626 of the radiation source 602 while the entire slip ring 616 remains stationary. This configuration can be used for CT scans. FIG. 7 is a side view of FIG. 6.

In FIG. 8, the configuration can be for a SPECT scan wherein the detectors 608 are shown dispersed and capable of rotating around the slip ring 616, in the direction of arrows 610.

Figure 9:
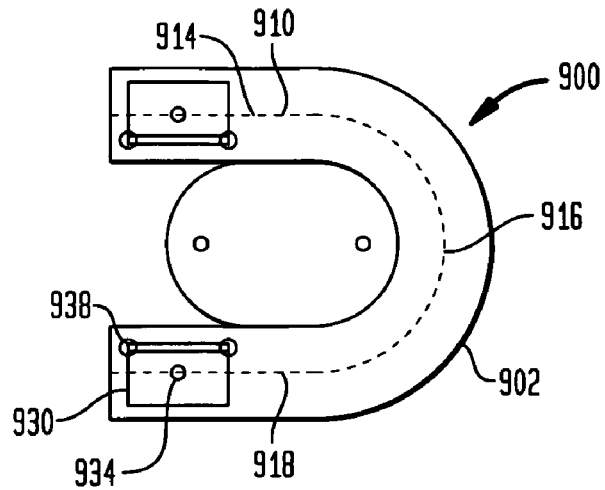
FIG. 9 is a cross-sectional top view of a U-shaped detector system in accordance with the present invention.
Figure 10:
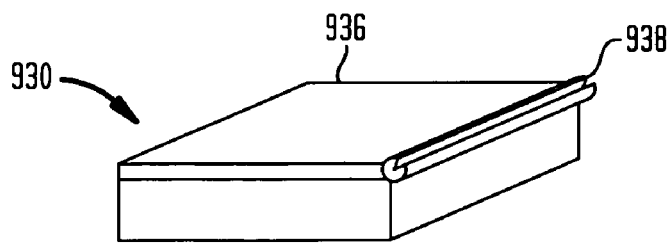
FIG. 10 is a perspective view of the mobile camera used in the detector system of FIG. 9 in accordance with the present invention.

In FIGS. 9 and 10 the detector system 900 is a U-shaped housing 902 having a single rail 916 with straight sections 914 and 918 and curved section 910, although double rails as in previous embodiments also can be used. The mobile camera unit 930 contains a detector 934 within a housing 936 configured to move on the rail 916. On the portion of the housing 936 facing the subject, the housing 936 has a transmission source 938 with swivel shielding that enables the directing of the field of emission impinging on the detector face.

The radiation source 938 for the U-shaped detector system 900 can be isotopes, or x-ray tubes or cold x-rays. The movement of the mobile camera units 930 will be dependent upon the type of detector 934 being used.

Figure 11:
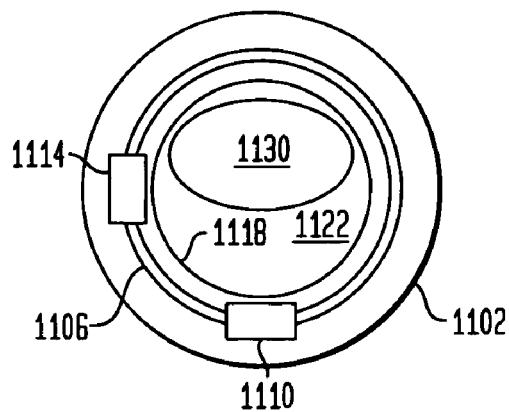
FIG. 11 is a cross-sectional top view of a circular detector system in accordance with the present invention.

In the embodiment illustrated in FIG. 11 the housing 1102 is circular with the subject 1130, positioned in the center 1122 facing inner end 1118. Within the housing 1102, there is a dual rail track 1106 that carries the detector containing mobile cameras 1114 and 1110. Alternatively, one of the mobile cameras, for example 1114, can contain a radiation source while the other mobile camera 1110 can contain a collimator and detectors.

Figure 12:
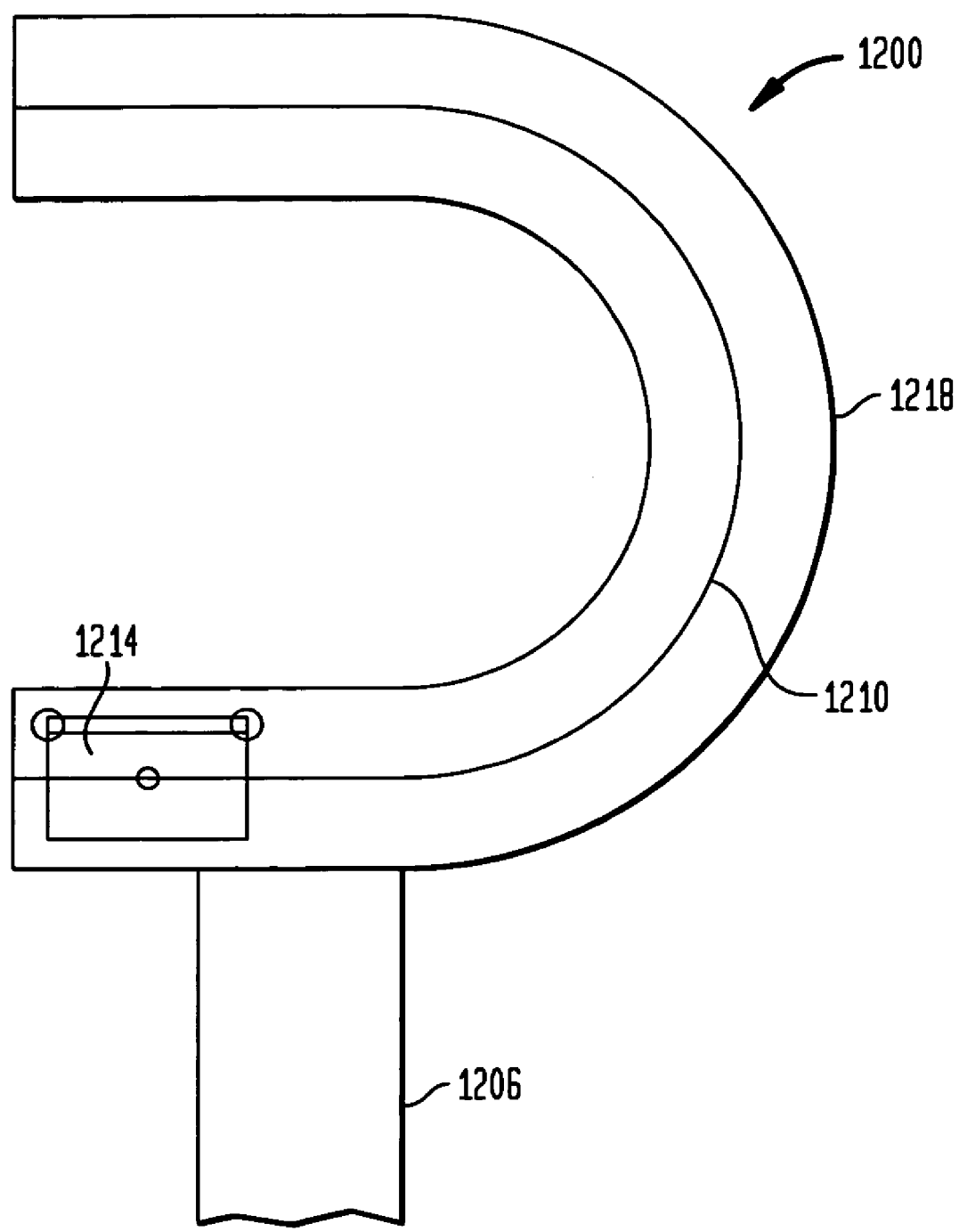
FIG. 12 is a cross-sectional side view of a C-shaped detector mounted on a stand in accordance with the present invention.

In FIG. 12, the detector system 1200 is positioned vertically on a stand 1206 to enable the detector system to be positioned on either side of the subject. In this illustration there is a single rail 1210 that carries the mobile camera 1214 within the housing 1218. Dual rails and multiple mobile cameras as discussed in conjunction with other embodiments can also be used in this embodiment. This embodiment enables the detector system 1200 to be beneficial for use in the lower body as well as for vaginal and rectal probes.

Figure 13:
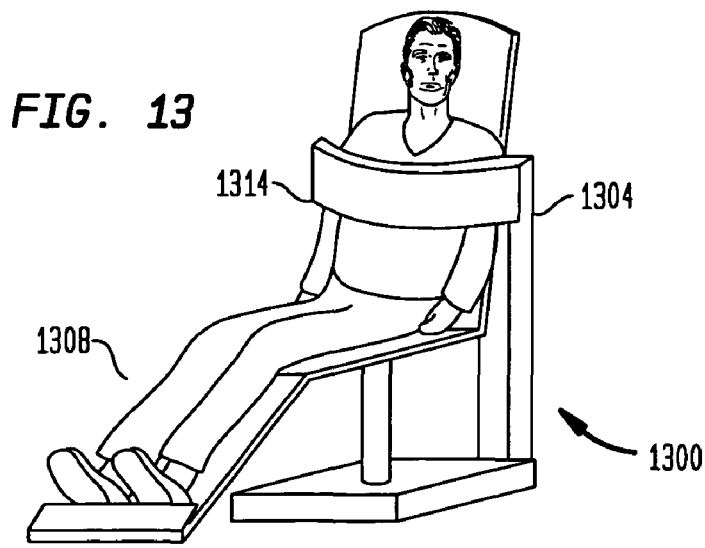
FIG. 13 is a perspective view of a person in a chair incorporating the detector unit of FIG. 1 in accordance with the present invention.

In FIG. 13 the detector unit 1300 consists of a chair 1304 designed to maintain the patient 1308 in the upright position. The detector housing 1314 is connected to the chair 1304 in a rotatable manner to enable the patent 1308 to sit in the chair 1304 with the detector housing 1314 being rotated and secured into place over the patient's 1308 chest.

Figure 14:
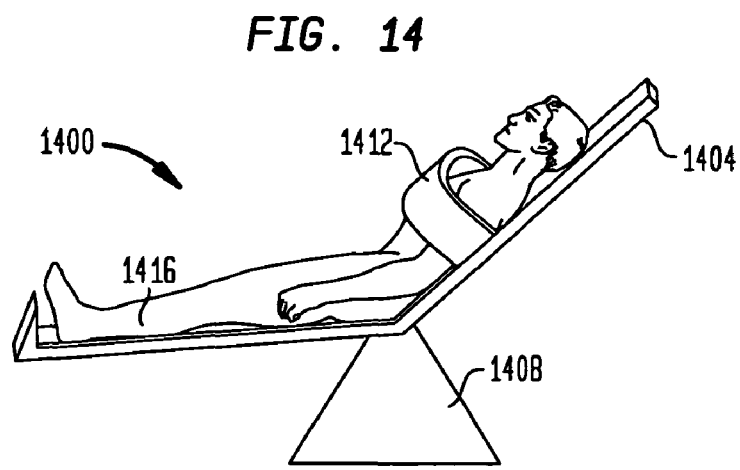
FIG. 14 is a side view of an alternate chair incorporating the detector unit of FIG. 1 in accordance with the present invention.

The chair 1404 in detector unit 1400 of FIG. 14 is designed to rotate upon base 1408 to enable the patient 1416 to be placed in any one of multiple positions. As described above, the detector housing 1412 rotates to enable the patient 1416 to lie on the chair 1404 prior to the housing 1412 being locked in place.

Figure 15:
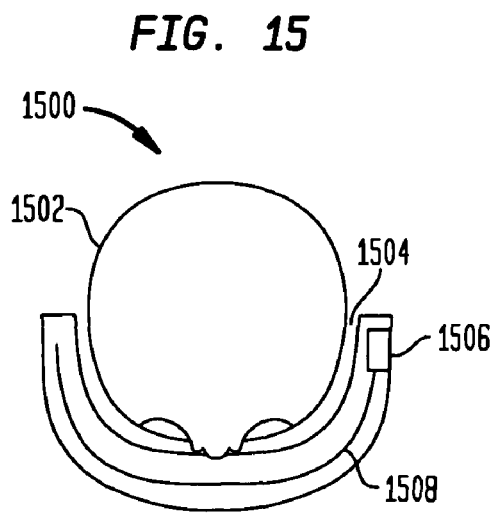
FIG. 15 is a top view of a detector unit dimensioned for use to treat oral disease in accordance with the present invention.

In FIG. 15 a detector unit 1500 is dimensioned for use to image oral cancer, an often-difficult area to treat due to the sizing requirements. The interior arc 1504 of the detector unit 1500 is dimensioned to bring the mobile camera 1506 in appropriate proximity to the patent's head 1502. The mobile camera 1506 runs on rails 1508 as described heretofore.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

What is claimed is:

1. A detector system for use in the detection of radiation photons in emission medical imaging, said detector system:
   a closed housing enclosing an internal area, said closed housing having a shape configured for imaging a particular selected organ of a patient;
   a pair of rails defining a co-planar rail path, said rails being fixed within said internal area, one rail aligned closer to the patient than the other;
   at least one mobile detector within said internal area, for detecting an emission photon source, the detector having at least one wheel abutting each of said respective rails for selective translation of the detector relative to the rails independent of the photon source;
   a turret interposed between said detector and rails, defining first and second planar ranges of motion about a pair of axes respectively oriented tangential and normal to said rail path;
   at least one driving mechanism, said at least one driving mechanism driving said at least one mobile detector along the rail path
   to a plurality of radiation photon receiving positions.

2. The detector system of claim 1, wherein said radiation photons are emitted from an isotope within a patient.

3. The detector system of claim 2, wherein said closed housing has an arced shape.

4. The detector system of claim 3, wherein said housing is dimensioned to substantially fit around a patient's chest.

5. The detector system of claim 4, wherein said housing is affixed to a chair.

6. The detector system of claim 3, wherein said housing is dimensioned to substantially fit around a portion of a patient's head.

7. The detector system of claim 3, wherein said housing is dimensioned to receive a portion of a patient's lower body.

8. The detector system of claim 3, wherein said housing is rotatably affixed to a stand.

9. The detector system of claim 1, wherein said radiation photons are emitted from a radioactive transmission source located within said closed housing.

10. The detector system of claim 1, wherein said pair of rails are spaced evenly apart from one another.

11. The detector system of claim 10, wherein said rails are at least partially flexible.

12. The detector system of claim 11, wherein said rails have a flexible region and a non-flexible region.

13. The detector system of claim 10, further comprising a plurality of mobile detectors carried on said pair of rails.

14. The detector system of claim 1, wherein said pair of rails are segmented into at least one flexible portion and at least one inflexible portion.

15. The detector system of claim 1, wherein a plurality of mobile detectors are mounted on said pair of rails.

16. The detector system of claim 15, wherein said plurality of mobile detectors are configured in a dispersed pattern.

17. The detector system of claim 16, wherein said plurality of mobile detectors are mounted on a slip ring.

18. The detector system of claim 1, wherein said mobile detector is a gamma camera.

19. The detector system of claim 1, wherein said detector system further comprises an ultrasonography detector.

20. The detector system of claim 1, wherein said mobile detector is selected from the group comprising solid-state detectors, crystals, and photomultiplier tubes.

21. The detector system of claim 1, further comprising a collimator selected from the group comprising parallel, focusing, multi-focusing, and variable focusing collimation.

22. The detector system of claim 1, wherein said mobile detector is a tomographic gamma camera for imaging a region from the group comprising cardiac, prostate, brain, extremity, and oral cancer imaging.

23. A mobile gamma camera system, comprising:
   a stationary closed housing having a shape configured for imaging a particular selected organ of a patient;
   a pair of rails defining a co-planar rail path mounted within said housing, one rail aligned closer to the patient than the other;
   a gamma camera within said housing, coupled to the rails by at least one wheel and capable of translation along said rail path;
   a turret interposed between said gamma camera and said pair of rails, defining first and second planar ranges of motion about a pair of axes respectively oriented tangentially and normal to said rail path;
   and
   a driver for moving said gamma camera along said rail path to preselected imaging angle positions within said housing.

24. The mobile gamma camera system of claim 23, wherein said stationary closed housing is arc-shaped.

25. The mobile gamma camera system of claim 23, wherein said stationary closed housing is U-shaped.

26. The mobile gamma camera system of claim 23, wherein said stationary closed housing is mounted to a patient chair.

27. The mobile gamma camera system of claim 23, wherein said stationary closed housing is dimensioned to fit around a portion of a patient's head.

28. A detector system for use in the detection of radiation photons in emission medical imaging, said detector system having:
   a closed housing enclosing an internal area, said closed housing having a shape configured for imaging a particular selected organ of a patient;
   at least one rail defining a planar rail path, said at least one rail being fixed within said internal area;
   at least one mobile detector within said internal area, for detecting an emission photon source, the detector having at least one wheel abutting the at least one rail for selective translation of the detector relative to the rail independent of the photon source, the detector oriented lateral to the planar rail path so that the detector is not interposed between the rail and a patient;
   a turret interposed between said detector and at least one rail, defining a first and second planar ranges of motion about a pair of axes respectively oriented tangentially and normal to said rail path;
   at least one driving mechanism, said at least one driving mechanism driving said at least one mobile detector along the rail path to a plurality of radiation photon receiving positions.

* * * * *